United States Patent [19]

Werle et al.

[11] Patent Number: 5,248,818
[45] Date of Patent: Sep. 28, 1993

[54] PROCESS FOR THE PRODUCTION OF CALCIUM FORMATE

[75] Inventors: Peter Werle, Gelnhausen; Martin Trageser, Gelnhausen-Hoechst; Ulrike Duderstadt, Hasselroth, all of Fed. Rep. of Germany

[73] Assignee: Degussa Aktiengesellschaft, Fed. Rep. of Germany

[21] Appl. No.: 856,649

[22] Filed: Mar. 24, 1992

[30] Foreign Application Priority Data

Apr. 25, 1991 [DE] Fed. Rep. of Germany ....... 4113470

[51] Int. Cl.$^5$ .............................................. C07C 53/06
[52] U.S. Cl. ................................................... 562/531
[58] Field of Search ......................................... 562/531

[56] References Cited

U.S. PATENT DOCUMENTS 3,864,369  2/1975  Isa et al. .................... 562/531 X
4,549,025  10/1985  Dalcanale et al. .......... 562/531 X

OTHER PUBLICATIONS

Soviet Inventions Illustrated, Week 8943, Dec. 1989, Derwent Publications Ltd., AN 89-315554 and SU-A-1474157 (English abstract) (mentioned on p. 3, line 20-p. 4, line 19).

"Calcium", Part B, No. 28, Verlag Chemie GmbH, pp. 160-162 (mentioned on p. 2, lines 9-12 of the present application) 1956.

Primary Examiner—Arthur C. Prescott
Attorney, Agent, or Firm—Beveridge, DeGrandi, Weilacher & Young

[57] ABSTRACT

Calcium formate is produced in aqueous phase by reaction of calcium hydroxide with formaldehyde in the presence of hydrogen peroxide or by reaction of calcium peroxide with formaldehyde. The molar ratio of CaO or Ca(OH)$_2$ to H$_2$CO to H$_2$O$_2$ is 1 to 2 to 1-1.2 and the molar ratio of CaO$_2$ to H$_2$CO is 1 to 2. Calcium formate is obtained in an almost substantially quantitative yield and in highly pure form. The process avoids the disadvantages of prior processes for the production of calcium formate from calcium hydroxide and formaldehyde.

17 Claims, No Drawings

PROCESS FOR THE PRODUCTION OF CALCIUM FORMATE

BACKGROUND AND INTRODUCTION

The present invention relates to a process for the production of calcium formate in aqueous phase by reaction of formaldehyde with calcium hydroxide in the presence of hydrogen peroxide or by reaction of formaldehyde with calcium peroxide.

Calcium formate, the calcium salt of formic acid, is presently obtained almost exclusively as a by-product in the manufacture of the polyhydric alcohols (polyols) pentaerythritol, trimethylol ethane, trimethylol propane and neopentyl glycol. It is formed during the reaction of 3-hydroxyaldehydes obtained by aldol condensation of formaldehyde in the presence of calcium hydroxide. Accordingly, calcium formate is the oxidation product of a mixed Cannizzaro reaction. Sodium formate is also obtained as a by-product in the manufacture of polyols.

Calcium formate is used for various purposes, for example as a tanning auxiliary, for the production of formic acid, as a setting accelerator in the cement industry, as a silaging auxiliary and, to an increasing extent, as a nutritive supplement in animal feeds. The last of these applications, where calcium formate is used to improve feed utilization, to reduce digestive problems, to avoid microbial feed decay (see brochure of Degussa AG, "Calciumformiat"-Ch 608-1-105-988 DD) imposes particular quality requirements to ensure that the feed containing calcium formate is not refused by the animals.

The disadvantages of producing calcium formate as a by-product of polyol synthesis is that an increase in the production of formate can only be obtained in connection with an increase in the production of the particular polyol (which presupposes corresponding marketing possibilities for the polyol).

It is also known that calcium formate can be produced by carbonylation of calcium hydroxide (cf., for example, Gmelin's Handbuch, Vol. Ca(B), pages 161-162 and Ullmann's Encyclopedia, 4th Ed., Vol. A 12, pages 23-24). These processes generally require technically complicated reactors, high pressures, high temperatures and generally long reaction times.

The Cannizzaro reaction of formaldehyde with strong inorganic bases takes place in accordance with the following scheme:

$$Me(OH)_n + 2n\ CH_2O \rightarrow Me(OOCH)_n + nCH_3OH$$

n=1 for Me=K, Na
n=2 for Me=Ca, Ba

The course of this reaction is determined by the metal hydroxide used. Numerous studies have shown that certain metal hydroxides do not promote the Cannizzaro reaction, but rather self-condensation of the formaldehyde. Although the formaldehyde molecule does not have an α-H atom and, accordingly, cannot enter into a normal aldol condensation, hydroxyaldehydes and ketones (particularly pentoses and hexoses, the so-called formoses) are formed by a substantially analogous reaction (T. Mizuno, A. Weiss, Adv. Carbohyd. Chem. Biochem. 29 173 (1974)). Formose-forming hydroxides include in particular $Pb(OH)_2$, $Sn(OH)_2$, $TlOH$ and $Ca(OH)_2$.

Accordingly, it has not hitherto been possible to isolate calcium formates in high yields by reaction of milk of lime, for example, with formaldehyde in accordance with the following equation:

$$Ca(OH)_2 + 4CH_2O \rightarrow Ca(OOCH)_2 + 2CH_3OH$$

because, after a certain incubation period dependent on the particular reaction temperature and on any impurities present, the self-catalytic formaldehyde condensation which begins at the same time converts any formaldehyde still present almost instantaneously into formoses in a highly exothermic reaction and thus removes it from the formate-forming reaction.

Russian patent 1474157 describes a process for the production of calcium formate by Cannizzaro reaction from calcium hydroxide and formaldehyde, in which saccharification of the formaldehyde is largely prevented by addition of the metal salts $MnSO_4$, $FeSO_4$, $Cu_2Cl_2$ or $Ce(NO_3)_2$. Although the yields of calcium formate obtained in this process are far better than the yields obtained in the absence of inhibitors, reaching around 89% in the best Example (Example 6), disadvantages lie in the very long reaction times (5 h), which cause poor volume/time yields, and the high dilutions which result in the cost-intensive evaporation of large quantities of water. In addition, the formaldehyde remaining in the solution (in Example 6, approximately 8% of the quantity used was not reacted) has to be separated from the calcium formate. This generally requires distillation under pressure on account of the particular properties of the formaldehyde. This incomplete reaction makes the basically simple Cannizzaro reaction unusable in this form for the synthesis of calcium formate on an industrial scale because the problem posed by the excess formaldehyde is not solved and calcium formate cannot be crystallized out from such solutions sufficiently free from formaldehyde. In addition, 2 mol methanol are obtained per mol calcium formate under the reaction conditions, leading on the one hand to a high input of formaldehyde and, on the other hand, to expense in removing the methanol from the reaction mixture.

SUMMARY OF THE INVENTION

An object of the present invention is to provide a process for the production of calcium formate in an economic manner without the disadvantages mentioned above.

According to the present invention, this and other objects are achieved by reaction of formaldehyde with a calcium compound in aqueous phase at a temperature of 20° to 90° C. and isolation of the formate from the aqueous phase, characterized in that the reaction is carried out in the presence of hydrogen peroxide and-/or calcium peroxide, calcium oxide or calcium hydroxide, formaldehyde and hydrogen peroxide in a molar ratio of 1 to 2 to 1-1.2 or calcium peroxide and formaldehyde in a molar ratio of 1 to 2 being used as reactants for the reaction.

DETAILED DESCRIPTION OF THE INVENTION

Without being bound by theory, the process according to the invention is based on the following reaction equations:

$$Ca(OH)_2 + 2H_2CO + H_2O_2 \rightarrow Ca(HCOO)_2 + H_2 + 2H_2O \quad (1)$$

$$CaO_2 + 2H_2CO \rightarrow Ca(HCOO)_2 + H_2 \quad (2)$$

According to equation (2), the peroxide undergoes hydrolysis in the aqueous phase with formation of $H_2O_2$ and $Ca(OH)_2$, so that the reactions according to (1) and (2) can even take place at the same time as one another. In practice, equation (2) may acquire significance for the production of calcium formate because calcium peroxide can also be formed in situ from $Ca(OH)_2$ and $H_2O_2$.

The reaction is carried out at temperatures of 20° C. to 90° C., preferably at temperatures of 30° C. to 70° C. and, more preferably, at temperatures of 40° C. to 60° C. The formation of so-called formoses from the saccharification of formaldehyde can be minimized by cooling the exothermic reaction to limit the temperature.

To carry out the reaction according to equation (1), an aqueous formaldehyde solution and an aqueous hydrogen peroxide solution may be simultaneously introduced into an aqueous solution or suspension of the calcium hydroxide. The addition is accompanied by thorough mixing, for example by stirring or pump-circulation of the reaction mixture. After they have been added, the reactants are left to react as and where necessary—the end of the reaction may readily be determined by determining the formaldehyde content. In one particularly preferred embodiment, calcium hydroxide and formaldehyde are initially introduced in aqueous phase and the hydrogen peroxide solution is subsequently added. The addition of a mixture of aqueous formaldehyde and hydrogen peroxide to an aqueous $Ca(OH)_2$ suspension or the introduction of $Ca(OH)_2$ into a mixture of aqueous formaldehyde and hydrogen peroxide is less preferred.

If the process according to the invention is carried out in accordance with equation (2), calcium peroxide is best introduced into an aqueous formaldehyde solution.

The formation of formoses, which is catalyzed by $Ca(OH)_2$ and hence can impair the production of calcium formate, may largely be avoided by additionally carrying out the reaction in the presence of suitable inhibitors. These inhibitors, which should not impair the desired reaction and should not complicate the recovery of pure formates, are various metal compounds and, in some cases, even metals in elemental form which are generally added to the reaction mixture before the actual reaction in a quantity of 0.1 mmol to 10 mmol per mol formaldehyde.

A person of ordinary skill in the art can obtain a rapid insight into the effectiveness of the metal salts as inhibitors by conducting a simple preliminary test. A mixture of $Ca(OH)_2$ and aqueous formaldehyde (37% by weight, unstabilized)—molar ratio 1:2—is stirred at 70° C. in the presence of the metal salt (for example 1 mmol per mol formaldehyde). The sudden appearance of a yellow coloration after a certain reaction time indicates that the formaldehyde has been consumed by formose formation. The following Table provides an overview of the inhibiting effect of various metal compounds.

TABLE

Activities of various inhibitors for inhibiting the formation of formoses

| Inhibitor | Stabilization (min.) | Inhibitor | Stabilization (min.) |
|---|---|---|---|
| None | 13 | $Mn_2O_3$ | 14 |
| LiBr | 13 | $MnSO_4$ | 29 |
| $KIO_4$ | 13 | $MnSO_4$ (3.8) | 21 |
| KSeCN | 13 | $MnCl_2$ | 45 |
| $SbCl_3$ | 14 | Mn(II) acetate | 90 |
| $Bi(NO_3)_2$ | 15 | Mn(III) acetate | 30 |
| $B_2O_3$ | 26 | Mn(II) acetyl- acetonate | 45 |
| $NaBO_2$ | 36 | | |
| $AlCl_3$ | 25 | $FeSO_4$ | 20 |
| $Al_2(SO_4)_3$ | 20 | $FeCl_3$ (3.8) | 20 |
| $TiCl_4$ | 16 | Co(III) acetate | 15 |
| $ZrCl_4$ | >90 | $NiSO_4$ | 14 |
| $ZrCl_4$ (3.8) | >90 | Cu powder (3.8) | 18 |
| $HfCl_4$ | 35 | $CuSO_4$ | 17 |
| $V_2O_5$ | 14 | $CuCl_2$ (3.8) | 21 |
| $VOSO_4$ | 20 | $Cu(NO_3)_2$ (3.8) | 26 |
| $NbCl_5$ | 20 | $AgNO_3$ | 14 |
| $K_2CrO_4$ | 15 | | |
| $Na_2MO_4$ | 24 | | |
| $Na_2WO_4$ | 51 | | |
| $WCl_4$ | 15 | | |

Test conditions: 15.2 $Ca(OH)_2$ (97%) + 32.5 g $CH_2O$ (37% by weight); T = 70° C.; r.p.m. = 200
Inhibitor input: 7.6 mg, based on central atom; tests with half the quantity of initiator (3.8 mg) were identified in the Table.

It can be seen from the Table that elements of one and the same group of the periodic system differ widely in their activity. For example, $C_4^{2-}$ is substantially ineffective while $WO_4^{2-}$ is a very effective inhibitor. Similarly, $TiCl_4$ is virtually ineffective while $ZrCl_4$ is among the most effective catalysts—oxide hydrates will be present in the reaction medium in this case. Even more surprising is the fact that differences even occur with one and the same element bound to different anions. This effect is particularly pronounced in the case of manganese. MnII acetate shows surprising inhibitor properties although it should be assumed that, irrespective of the manganese salt selected, Mn hydroxides are uniformly present in the alkaline reaction medium.

Suitable inhibitors are salts selected from the group consisting of $CuCl_2$, $Cu(NO_3)_2$, $MnCl_2$, $MnSO_4$, Mn(II) acetate, Mn(II) acetyl acetonate, Mn(III) acetate; molybdates and, in particular, tungstates of the alkali and alkaline earth metals; $ZrCl_4$, $ZrOCl_2$, $HfCl_4$; borates of the alkali and alkaline earth metals; and $AlCl_3$. Manganese salts, zirconium halides and tungstates have an outstanding effect. Additions of the highly effective inhibitors in the range from 0.1 to 2 mmol per mol formaldehyde are generally sufficient. If necessary, the reaction may even be carried out in the presence of a small quantity of foam inhibitor known in the art, for example a silicone-based product, to prevent the reaction mixture from foaming.

The reaction of the calcium hydroxide with formaldehyde and hydrogen peroxide and the reaction between calcium peroxide and formaldehyde gives substantially water-clear formate solutions which only contain traces of free formaldehyde because the formaldehyde conversion generally exceeds 95% and, under optimized conditions, is generally above 98%. Before the formate is isolated from the aqueous reaction solution, the pH value is if necessary adjusted to pH 6.5 to 7.5 by addition of formic acid. Should the solution still contain suspended material because of secondary constituents in the oxide, hydroxide or peroxide used (this would appear mostly to be the case where lime is used for the production of calcium formate), this suspended material may be removed in the usual way with or without filter aids. The formate is isolated from the clear solution by methods known in the art, for example by evaporation crystallization, separation of the crystals from the mother liquor and drying of the crystals.

In the process according to the present invention, the total quantity of water is kept so small that the formate solution obtained is highly concentrated and the energy consumed in isolating the formate is minimal. Formaldehyde is generally used in the form of a commercially available aqueous solution, more particularly with a content of 37% by weight. In principle, it is also possible to use formaldehyde oligomers having the formula $HO-(CH_2O)_nH$ with $n=10$ to 30 providing the actual reaction is preceded by depolymerization. Aqueous hydrogen peroxide may be used in any concentration and is best used in its typical commercial concentration, more particularly between 30 and 70% by weight. According to the invention, the total quantity of water may also be gauged in such a way that, on completion of the reaction, the reaction solution contains less water than corresponds to the solubility of the calcium formate. Accordingly, metastable formate solutions are present and enable the energy consumed in isolating the formate to be further reduced.

The process according to the invention enables calcium formate to be produced in a substantially quantitative yield and, in addition, in highly pure form and with high volume/time yields. The process may be carried out discontinuously or continuously. In terms of equipment, the process is simple because the volume/time yield is high and surprisingly the reaction solution only contains traces of unreacted formaldehyde so that there is no need for pressure distillation to remove formaldehyde. In contrast to the typical Cannizzaro reaction, surprisingly only 2 mol formaldehyde per mol Ca compound are required in the process according to the invention (as opposed to the four mol in the Cannizzaro reaction), in addition to which no methanol is formed and therefore does have to be distilled off. In addition, the hydrogen formed during the reaction can be burnt and hence used to generate energy and thus to reduce the process costs.

EXAMPLES

Example 1

76.4 calcium hydroxide (97% by weight; 1 mol), 600 ml water, 0.200 g zirconium tetrachloride (0.0076 mol) and 162.5 g formaldehyde (37% by weight; 2 mol) are introduced into a reactor equipped with a stirrer and gas outlet pipe at a temperature of around 40° to 50° C. 120 g $H_2O_2$ (30% by weight; 1.05 mol) are then added dropwise over a period of 30 minutes with intensive cooling. The temperature is kept at max. 50° C. The reaction mixture is then stirred for 15 minutes, the pH value of the solution falling to around 7-7.5, and the insoluble lime constituents (gangue) are filtered off. 1020 ml (increase in volume through addition of washing water) of a clear colorless solution are obtained. Compexometric determination reveals 126 g calcium formate, i.e. 97% of the theoretical. The residual formaldehyde content is 0.07%. Concentration of the solution by evaporation and drying gives crystalline colorless calcium formate in a purity of 99.7% (as determined by removal of the Ca ions using a strongly acidic cationic exchanger and titration of the formic acid released, a method known in the art).

Example 2

The procedure is as in Example 1 using 0.230 g manganese(II) acetate. $2H_2O$ (0.00086 mol) as inhibitor. 1020 ml of a clear solution having a pH value of 7.6 are obtained from the pale brownish reaction mixture after filtration. The residual formaldehyde content is 0.08%. Titration reveals 125 g calcium formate (96% of the theoretical).

EXAMPLE 3

38.2 g lime (97% by weight) are introduced into 300 ml water and 0.25 g $NaBO_2.4 H_2O$ (0.0018 mol) and 81 g formaldehyde (37% by weight) are added. 30% by weight $H_2O_2$ is added dropwise over a period of 15 minutes at a maximum temperature of up to 60° C., followed by stirring for 30 minutes and filtration. 475 ml of a colorless solution having a pH value of 7.2 and a residual formaldehyde content of 0.06% are obtained. Yield of calcium formate: 62.0 g=95.3% of the theoretical.

EXAMPLE 4

152.8 g lime (97% by weight, 2.0 mol) are initially introduced into 1200 ml water, after which 324.0 g formaldehyde (37% by weight, 4.0 mol) and 240 g $H_2O_2$ (30% by weight, 2.1 mol) are separately added dropwise over a period of about 30 minutes while cooling in an ice bath and while nitrogen is passed through. The temperature is limited to 50° to 55° C. The mixture is then stirred for 30 minutes at 40° to 50° C. The solution, which has a pH value of about 10, is adjusted to pH 7 with 2 ml formic acid and filtered after the addition of a little kieselguhr. 1880 ml of a clear solution containing 250 g calcium formate are obtained. The residual formaldehyde content is somewhat higher in this case at 0.1%.

EXAMPLE 5

150 ml water and 81 g formaldehyde (37% by weight, 1.0 mol) are initially introduced at room temperature. 60.1 g calcium peroxide (60% by weight, 0.5 mol) are introduced into this solution, followed by stirring for 2 h at 40° C. A foam inhibitor has to be added. The strongly alkaline suspension is filtered and neutralized with 0.7 ml formic acid. 455 ml of a clear colorless solution are obtained. Formaldehyde content <0.1%.

EXAMPLE 6

The addition of a mixture of formaldehyde and hydrogen peroxide is less suitable for obtaining a low residual formaldehyde content. A mixture of 400 ml $H_2O$, 162 g formaldehyde (37% by weight) and 120 g $H_2O_2$ (30% by weight) is added to 76.4 g $Ca(OH)_2$ (97% by weight) and 200 ml $H_2O$ plus a few drops of a silicone-based foam inhibitor. The reaction is initiated at room temperature and the reaction temperature is kept by cooling at 50° to 55° C. The mixture added is run in over a period of 30 minutes, followed by an after-reaction lasting 30 minutes. The fully reacted solution has pH value of 12 and is then neutralized by addition of 3.5 ml formic acid. The clear filtrate still contains 0.6% free formaldehyde which has to be reduced to around 0.1% before working up to calcium formate.

Example 7

76.4 g lime (97% by weight) are initially introduced in 400 ml water and 0.05 g $H_2WO_4$ (0.0002 mol) and 162 g formaldehyde (37% by weight) are then added. 72 g 50% by weight $H_2O_2$ are added dropwise over a period of 15 minutes at max. 50° C., followed by stirring for 30 minutes and filtration. 710 g of a colorless solution oversaturated with calcium formaldehyde are obtained: residual formaldehyde content 0.07%, calcium formate content 17.8% by weight (solubility of Ca formate in $H_2O=14\%$ by weight).

Further modifications and variations of the foregoing will be apparent to those skilled in the art and are intended to be encompassed by the claims appended hereto.

German priority application P 41 13 470.2 is relied on and incorporated herein by reference.

What is claimed:

1. A process for the production of calcium formate by reaction of formaldehyde with a calcium compound in aqueous phase, said process comprises reacting (a) hydrogen peroxide with formaldehyde and calcium oxide or calcium hydroxide or (b) calcium peroxide and formaldehyde, at a temperature of 20° of 90° C., and isolating said formate from said aqueous phase.

2. The process according to claim 1, wherein the molar ratio in (a) of calcium peroxide or calcium hydroxide:formaldehyde:hydrogen peroxide is 1:2:1 to 1.2.

3. The process according to claim 1, wherein the molar ratio in (b) of calcium peroxide:formaldehyde is 1:2.

4. The process according to claim 1, wherein said temperature is 30° to 70° C.

5. The process according to claim 4, wherein said temperature is 40° to 60° C.

6. The process according to claim 1, wherein the yield of said formate is at least 95%.

7. The process according to claim 6, wherein the yield of said formate is at least 98%.

8. The process according to claim 1, wherein the amount of formaldehyde after said reaction is less than or equal to 0.1%.

9. The process according to claim 1, wherein in (a) said calcium hydroxide and formaldehyde are added to said hydrogen peroxide.

10. The process according to claim 1, wherein in (a) the concentration of said hydrogen peroxide is 30 to 70% by weight.

11. The process according to claim 1, wherein said reaction is carried out in the presence of 0.1 to 10 mmol of inhibitor per mol formaldehyde.

12. The process according to claim 11, wherein said inhibitor is at least one member selected from the group consisting of $CuCl_2$, $Cu(NO_3)_2$, $MnCl_2$, $MnSO_4$, Mn(II) acetate, Mn(II) acetyl acetonate, Mn(III) acetate; molybdates and tungstates of the alkali and alkaline earth metals; $ZrCl_4$, $ZrOCl_2$, $HfCl_4$; borates of the alkali and alkaline earth metals; and $AlCl_3$.

13. The process according to claim 11, wherein said inhibitor is at least one member selected from the group consisting of manganese salts, zirconium halides and tungstates.

14. The process according to claim 1, further comprising adjusting the pH to a range of 6.5 to 7.5.

15. The process according to claim 1, wherein in (b) said calcium peroxide is introduced into an aqueous solution of said formaldehyde.

16. The process according to claim 1, wherein said reaction is carried out in the presence of 0.1 to 2 mmol of inhibitor per mol formaldehyde.

17. A process for the production of calcium formate by reaction of formaldehyde with a calcium compound in aqueous phase, said process comprises reacting hydrogen peroxide and/or calcium peroxide with formaldehyde, wherein (a) calcium oxide or calcium hydroxide, formaldehyde and hydrogen peroxide are present in a molar ratio of 1:2:1 to 1.2, or (b) calcium peroxide and formaldehyde are present in a molar ratio of 1:2, at a temperature of 20° to 90° C., and isolating said formate from said aqueous phase.

* * * * *